(12) United States Patent
Mizutani et al.

(10) Patent No.: US 9,012,211 B2
(45) Date of Patent: Apr. 21, 2015

(54) HARVESTED SAMPLE PREPARATION PERSONAL BOX AND SYSTEM AND METHOD OF HARVESTED SAMPLE PREPARATION

(75) Inventors: Manabu Mizutani, Tokyo (JP); Yoshiko Nohmi, Tokyo (JP); Kenji Yoneda, Kanazawa (JP)

(73) Assignees: Cellseed Inc., Shinjuku-ku, Tokyo (JP); Shibuya Kogyo Co., Ltd., Kanazawa-shi, Ishikawa (JP)

( * ) Notice: Subject to any disclaimer, the term of this patent is extended or adjusted under 35 U.S.C. 154(b) by 534 days.

(21) Appl. No.: 13/376,973

(22) PCT Filed: Jun. 22, 2010

(86) PCT No.: PCT/JP2010/060534
§ 371 (c)(1),
(2), (4) Date: Dec. 8, 2011

(87) PCT Pub. No.: WO2010/150773
PCT Pub. Date: Dec. 29, 2010

(65) Prior Publication Data
US 2012/0077220 A1 Mar. 29, 2012

(30) Foreign Application Priority Data
Jun. 23, 2009 (JP) ................................. 2009-148743

(51) Int. Cl.
*C12M 1/00* (2006.01)
*C12M 3/00* (2006.01)
*C12M 1/22* (2006.01)
*A61B 10/00* (2006.01)
*C12M 1/12* (2006.01)

(52) U.S. Cl.
CPC ............ *C12M 45/22* (2013.01); *A61B 10/0096* (2013.01); *C12M 37/00* (2013.01)

(58) Field of Classification Search
USPC ............................................ 435/283.1–309.4
See application file for complete search history.

(56) References Cited

U.S. PATENT DOCUMENTS

| 4,696,902 A * | 9/1987 | Bisconte .................... 435/286.2 |
| 2003/0040104 A1 * | 2/2003 | Barbera-Guillem ....... 435/286.2 |

FOREIGN PATENT DOCUMENTS

| JP | 2004-016094 | 1/2004 |
| JP | 2004-286568 | 10/2004 |
| JP | 2005-013096 | 1/2005 |

(Continued)

OTHER PUBLICATIONS

PCT/JP2010/060534 International Search Report (2 pages).

*Primary Examiner* — Nathan Bowers
*Assistant Examiner* — Lydia Edwards
(74) *Attorney, Agent, or Firm* — Flynn, Thiel, Boutell & Tanis, P.C.

(57) ABSTRACT

A harvested sample preparation system includes an operation isolator 3 in which aseptic manipulation is executed, a harvested sample preparation personal box 4 which can be connected with the operation isolator 3 and a storage 5 that stores a plurality of harvested sample preparation personal boxes 4. The harvested sample preparation personal box 4 includes a first housing chamber 4Aa and a second housing chamber 4Ab, and a fluid appropriate for cell culturing is supplied to the first housing chamber 4Aa from a fluid supply pipe 16 included by the storage 5 while cooling fluid is supplied to the second housing chamber 4Ab from a cooling fluid supply pipe 18. The harvested sample preparation system that prevents mix-up and cross-contamination with a simple configuration can be provided.

2 Claims, 4 Drawing Sheets

(56) References Cited

FOREIGN PATENT DOCUMENTS

| | | |
|---|---|---|
| JP | 2005-185105 | 7/2005 |
| JP | 2005-278566 | 10/2005 |
| JP | 2005-304439 | 11/2005 |
| JP | 2006-149232 | 6/2006 |
| JP | 2006-296296 | 11/2006 |
| JP | 2008-237046 | 10/2008 |
| JP | 2009-513127 | 4/2009 |
| WO | WO 2007049078 A1 * | 5/2007 |
| WO | WO 2007-102399 | 9/2007 |

* cited by examiner

HARVESTED SAMPLE PREPARATION PERSONAL BOX AND SYSTEM AND METHOD OF HARVESTED SAMPLE PREPARATION

TECHNICAL FIELD

The present invention relates to a harvested sample preparation personal box and a system and a method of harvested sample preparation. More specifically, it relates to a harvested sample preparation personal box used in preparation of a harvested sample collected from a donor in the field of regenerative medicine for housing a harvested sample from a single donor and an article related to this harvested sample and a system and a method of harvested sample preparation using this harvested sample preparation personal box.

BACKGROUND ART

In the field of regenerative medicine, where a cell, a tissue or the like collected from a donor is cultured and processed to recover or regenerate a lost tissue, organ or the like, there is a problem that a mix-up of cells, donor-derived reagents and the like among a plurality of donors and cross-contamination of cells derived from different donors should be prevented. As a system to solve such problem, Patent Literature 1 is proposed.

A system of Patent Literature 1 (mix-up prevention system) is constituted by a plurality of incubators and drug refrigerators, each having an electronic key, a personal computer that collectively manages the electrical key, a driver unit to open and close the electronic key, a barcode scanner and a barcode issuing machine. A barcode corresponding to a culture vessel and a medium storing bottle of one donor is attached to a process instruction, and the personal computer controls the operation such that the electronic key of each incubator and drug refrigerator housing the culture vessel and the medium storing bottle are opened and closed by reading this barcode.

PRIOR ART DOCUMENTS

Patent Literature

Patent Literature 1: Japanese Patent Laid-Open No. 2005-304439

SUMMARY OF INVENTION

Problems to be Solved by the Invention

As stated above, in the mix-up prevention system of Patent Literature 1, the electronic keys have to be provided to all the incubators and the drug refrigerators, and a system for collectively managing these components should be established. Moreover, since the culture vessel and the medium storing bottle have to be taken out of an operation space such as a safety cabinet to be stored in the incubators and the drug refrigerators, maintaining the entire space where the incubators, drug refrigerators and safety cabinet are disposed at a high cleanliness level is required.

An object of the present invention is to provide a harvested sample preparation personal box and a system and a method of harvested sample preparation that prevent mix-up or cross-contamination among a plurality of donors reliably with a simple configuration.

Means for Solving the Problems

In view of the above circumstances, the first embodiment of the present invention is to provide a harvested sample preparation personal box including:

a housing part main body in which a closed space is formed;

a lid body that hermetically closes the housing part main body; and connecting means that connects an isolator in which aseptic manipulation is executed with the housing part main body to communicate between the isolator and the housing part main body, wherein the housing part main body includes a plurality of independent closed spaces, at least one constituting a first housing chamber for housing a harvested sample collected from a single donor and the other constituting a second housing chamber for housing an article related to the harvested sample, and the housing part main body includes identifying means that identifies itself from other housing part main bodies.

Moreover, the second embodiment of the present invention is to provide a harvested sample preparation system including:

an isolator in which aseptic manipulation is executed;

a harvested sample preparation personal box which can be connected with this isolator and whose inner portion can be hermetically sealed; and storing means that stores a plurality of harvested sample preparation personal boxes, wherein the harvested sample preparation box includes a plurality of independent closed spaces, at least one including a supply port constituting a first housing chamber for housing a culture vessel in which a harvested sample collected from a single donor is seeded and the other constituting a second housing chamber for housing an article related to the harvested sample housed in the first housing chamber, and the storing means includes culture fluid supply means that provides fluid appropriate for culture to the first housing chamber through the supply port.

Further, the third embodiment of the present invention is to provide a harvested sample preparation method including the steps of:

preparing a plurality of harvested sample preparation personal boxes including a plurality of hermetically-sealable independent closed spaces;

connecting any of the harvested sample preparation personal boxes with an isolator in which aseptic manipulation is executed;

housing a culture vessel in which a harvested sample collected from a single donor is seeded in at least one closed space;

housing an article related to the housed harvested sample in the other closed space;

separating the harvested sample preparation personal box from the isolator;

supplying fluid appropriate for culture to the closed space that houses the culture vessel to culture the harvested sample;

providing cool fluid to the closed space that houses the article related to the harvested sample to refrigerate the article;

decontaminating an inner portion of the isolator after the isolator is separated from the harvested sample preparation personal box; and connecting a different harvested sample preparation personal box with the isolator to handle a harvested sample collected from a different donor.

Advantageous Effect of Invention

According to the harvested sample preparation personal box and a system and a method of harvested sample preparation using this harvested sample preparation personal box, a harvested sample collected from a single donor and an article related to this harvested sample can be housed in a single housing part main body. Moreover, since this harvested sample preparation personal box can be connected with an isolator, a preparation operation of the harvest sample can be executed while mix-up or cross-contamination among a plurality of donors is prevented reliably with a simple configuration.

MODE FOR CARRYING OUT THE INVENTION

Figure 1:
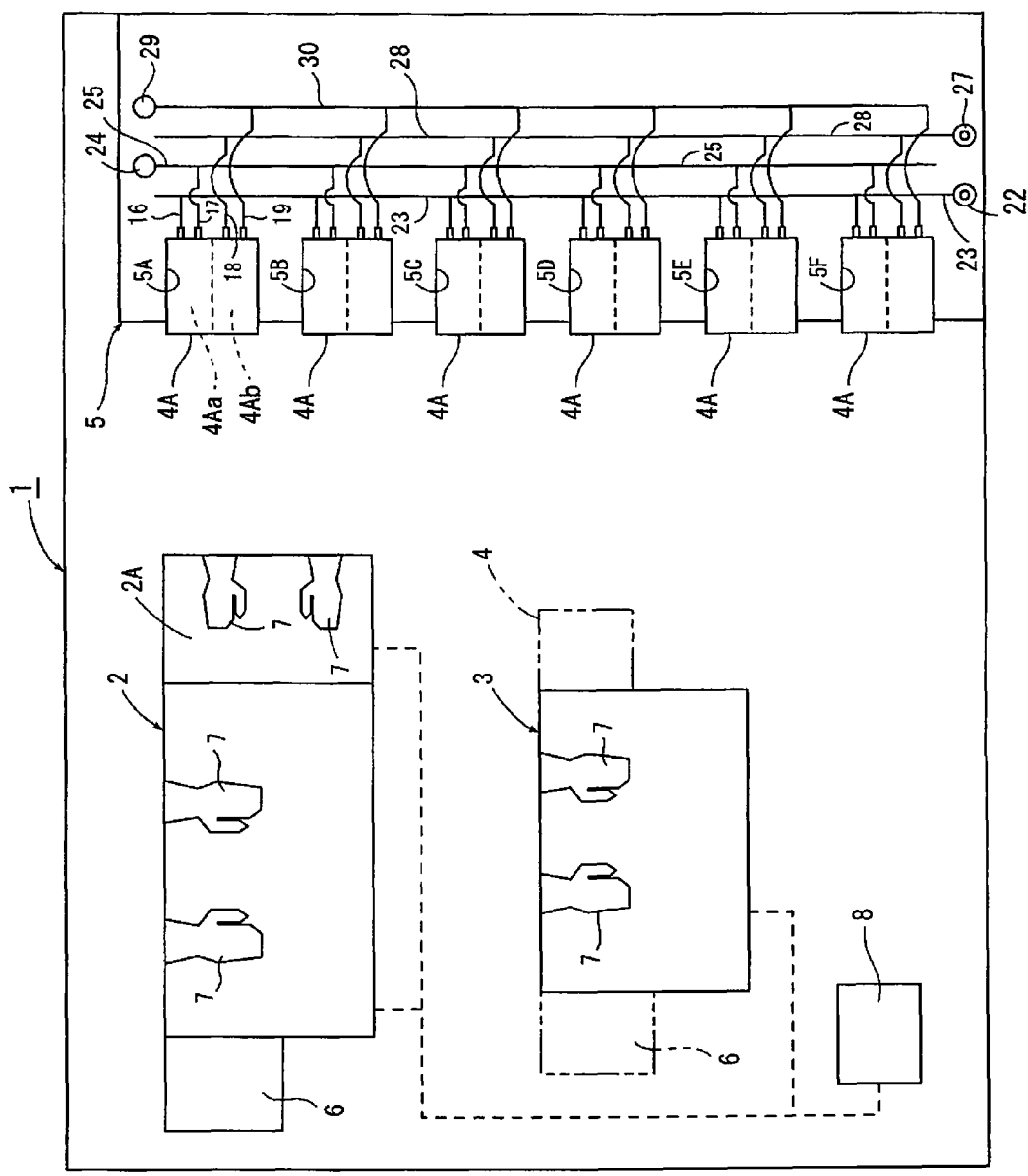
FIG. 1 is a configuration diagram of a harvested sample preparation system showing an embodiment according to the present invention.

Hereinafter, the present invention will be explained regarding a shown embodiment. In FIG. 1, the reference numeral 1 denotes a preparation operation room where a harvested sample preparation system according to the present invention is installed, and a preparation operation, for regenerative medicine use, of harvested samples such as a cell and a tissue collected from a human being for regenerative medicine use is executed in this preparation operation room 1.

In the preparation operation room 1, a stocker isolator 2 that stocks materials such as a common container which is necessary for preparation of a harvested sample, reagents and the like in a sterile condition, an operation isolator 3 that performs seeding, media replacement and passage operation of cells and processing operation of a cell or the like in a sterile condition, a plurality of harvested sample preparation personal boxes 4 (six in the example of FIG. 1) which is attachable to and removable from the operation isolator 3 while mutually maintaining an internal sterile condition and storing means 5 that houses each harvested sample preparation personal box 4 for storing are disposed. The preparation operation room 1 is maintained to a cleanliness of class 100,000 or more. The operation isolator 3, the harvest sample preparation personal box 4 and the storing means 5 constitute a harvested sample preparation system.

The stocker isolator 2 includes a pass-box with decontamination 2A that decontaminates an exterior package of aseptic-pack materials, reagents and the like and a transfer box 6 that delivers the materials, the reagents and the like from the stocker isolator 2 while maintaining a sterile condition. Moreover, gloves 7 for operation of an operator are provided on a desired position of the stocker isolator 2.

The stocker isolator 2 is constituted such that its inner portion is maintained at positive pressure, and by providing a decontamination medium from a decontamination apparatus 8, the inner portion is decontaminated and a sterile condition is maintained. Moreover, the pass-box with decontamination 2A decontaminates exterior packages of materials, reagents and the like housed in the pass-box with decontamination 2A by the decontamination medium provided from the decontamination apparatus 8. As the decontamination medium provided from the decontamination apparatus 8, hydrogen peroxide, formaldehyde, peracetic, ozone, chlorine dioxide and the like are listed, and vapor, gas or mist of these media are provided as decontamination gas. Communication or blocking between the stocker isolator 2 and the pass-box with decontamination 2A can be executed. Moreover, the transfer box 6 can be connected with the stocker isolator 2 by RTP (Rapid Transfer Port), and their inner portions can communicate with each other in a state in which they are blocked from the external atmosphere. Additionally, an operation robot may be provided in the stocker isolator 2 to make it unattended.

Figure 2:
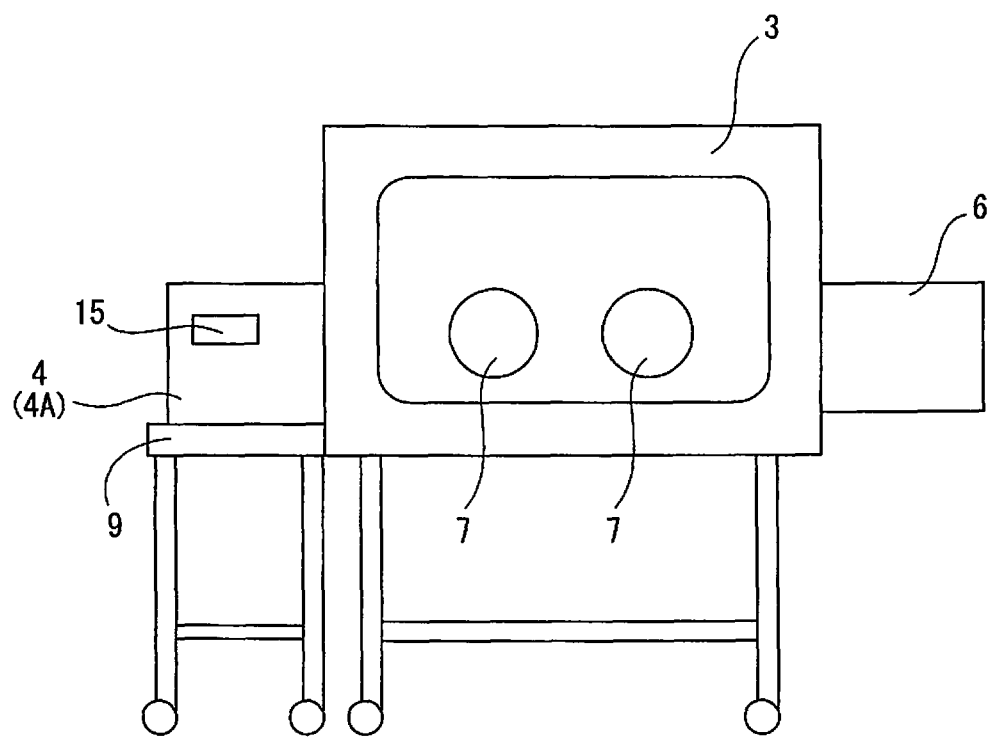
FIG. 2 is a front view showing a state that a harvested sample preparation personal box is connected with an operation isolator.

As shown in FIG. 2, the operation isolator 3 can be connected with the harvested sample preparation personal box 4 as well as the transfer box 6. Moreover, the operation isolator 3 maintains its inner portion at positive pressure in the same manner as the stocker isolator 2, and by providing the decontamination medium from the decontamination apparatus 8, the inner portion is decontaminated to maintain a sterile condition. In addition, in a state of communication with the harvested sample preparation personal box 4, an inner portion of the operation isolator 3 can also be decontaminated. The harvested sample preparation personal box 4 can be moved when it is disposed on moving means 9 such as a wagon, and in the disposed state it is connected with the operation isolator 3 to maintain a connected state. Additionally, the gloves 7 are also provided to the operation isolator 3 in the same manner as the stocker isolator 2.

Figure 3:
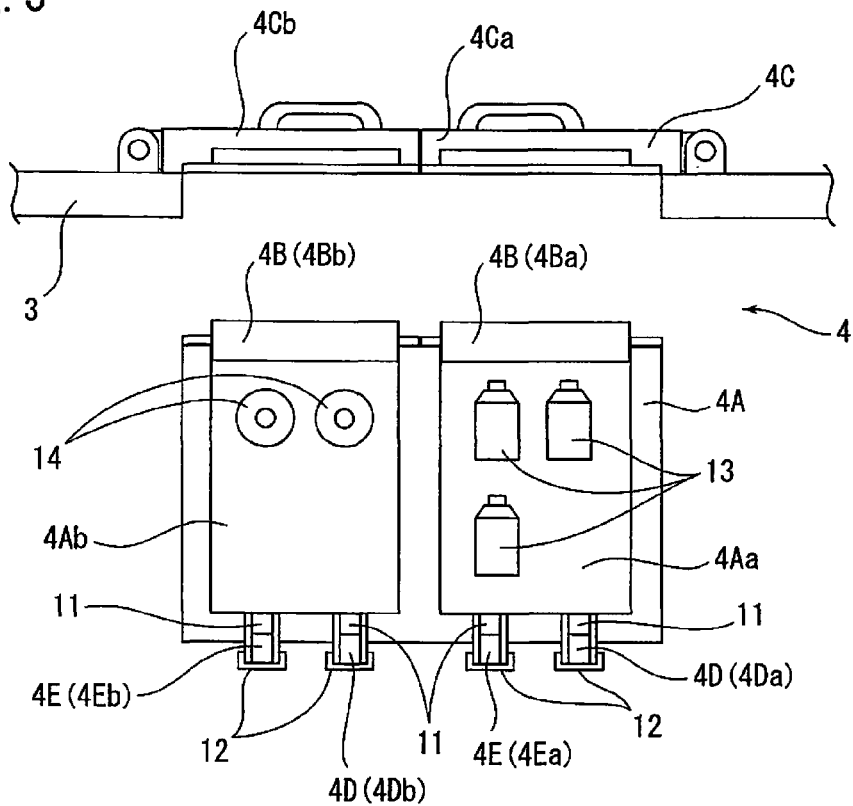
FIG. 3 is a cross-sectional view showing the configuration of the harvested sample preparation personal box showing an embodiment according to the present invention.

As shown in FIG. 3, the harvested sample preparation personal box 4 is constituted by a housing part main body 4A in which a closed space is formed, a lid body 4B that hermetically seals the housing part main body 4A and connecting means 4C that connects the housing part main body 4A with the operation isolator 3 that executes the aseptic manipulation to communicate between the operation isolator 3 and the housing part main body 4A.

The housing part main body 4A has an inner portion partitioned into two independent closed spaces, one constitutes a first housing chamber 4Aa for housing a harvested sample collected from a single donor and the other constitutes a second housing chamber 4Ab for housing an article related to the harvested sample. The first housing chamber 4Aa is hermetically closed by a first lid body 4Ba, and the second housing chamber 4Ab is hermetically closed by a second lid body 4Bb. In addition, the first lid body 4Ba and the second lid body 4Bb include main body parts that are fitted to apertures of the first housing chamber 4Aa and the second housing chamber 4Ab, respectively, and flange portions that cover the circumference of the apertures exposed to the operation isolator 3 when the first housing chamber 4Aa and the second housing chamber 4Ab communicate with the operation isolator 3.

Figure 4:
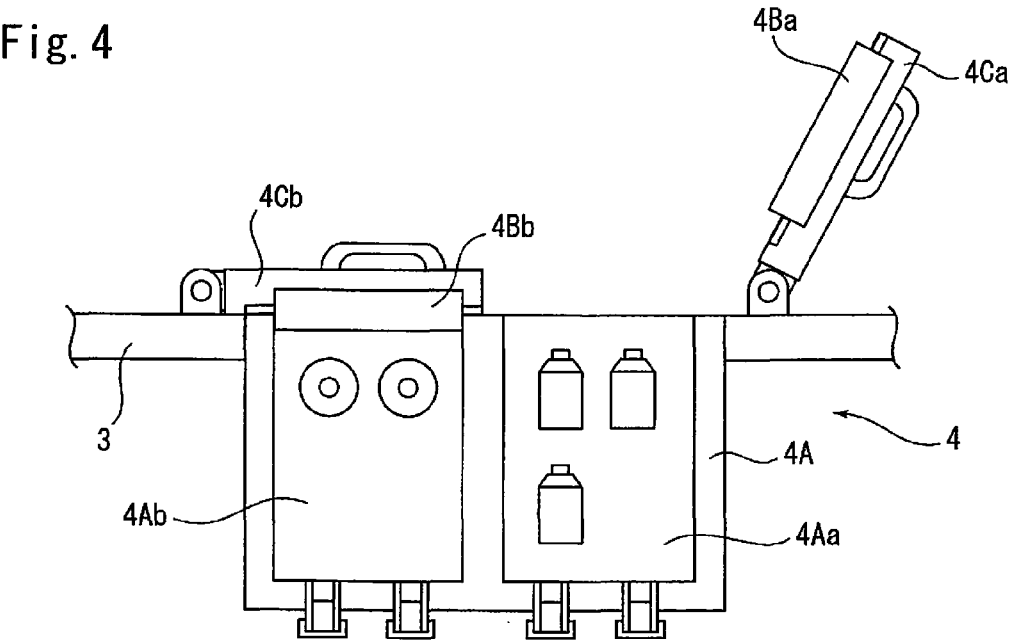
FIG. 4 is a cross-sectional view showing a state that the harvested sample preparation personal box is connected with the operation isolator.

The connecting means 4C is provided on an aperture formed on a wall of the operation isolator 3, and includes a first connection lid 4Ca to which the first lid body 4Ba is fitted and a second connection lid 4Cb to which the second lid body 4Bb is fitted. The first connection lid 4Ca and the second connection lid 4Cb hermetically close the aperture formed on the wall of the operation isolator 3, and with integral incorporation of the first lid body 4Ba into the first connection lid 4Ca and the second lid body 4Bb into the second connection lid 4Cb, the housing part main body 4A is connected with the operation isolator 3. Moreover, as shown in FIG. 4, the first connection lid 4Ca or the second connection lid 4Cb is opened to an inner portion of the operation isolator 3 in a state that the first lid body 4Ba and the second lid body 4Bb are fitted, the first housing chamber 4Aa and the second housing chamber 4Ab in the housing part main body 4A communicate with an inner portion of the operation isolator 3 in a blocked state from the outside. In such a case, external surfaces of the first lid body 4Ba and the second lid body 4Bb exposed to the external atmosphere are covered by the first connection lid 4Ca and the second connection lid 4Cb. With this configuration, the operation isolator 3 and the housing part main body 4A of the harvested sample preparation personal box 4 can be connected with and separated from each other while a sterile condition of their inner portions are maintained. Such connecting means 4C is commonly used in each harvested sample preparation personal box 4.

The housing part main body 4A and the lid body 4B are constituted by insulator materials, and in the closed spaces, a supply port 4D for supplying fluid and a discharge port 4E for discharging fluid are respectively provided corresponding to the first housing chamber 4Aa and the second housing chamber 4Ab. In the supply port 4D and the discharge port 4E, gas appropriate for a cell culture is supplied as the fluid from a supply port 4Da provided in the first housing chamber 4Aa, and it is discharged from a discharge port 4Ea. Moreover, cooled gas is supplied as the fluid from a supply port 4Db provided in the second housing chamber 4Ab to cool an inner portion of the second housing chamber 4Ab, and it is discharged from a discharge port 4Eb. To the supply port 4D and the discharge port 4E, a sterile filter 11 such as an HEPA filter is respectively provided, and caps 12 covering the supply port 4D and the discharge port 4E are respectively attached, and in the absence of supply and discharge of the fluid, these ports are hermetically closed by the caps 12.

A cell or a tissue can be listed as a harvested sample collected from a single donor to be housed in the first housing chamber 4Aa, and they are seeded in a medium of a culture vessel 13 and housed in the first housing chamber 4A to be cultured. Gas appropriate for a cell culture such as carbon dioxide is listed as the gas supplied from the supply port 4Da, and the gas is supplied after it is heated to a temperature appropriate for the culture and discharged from the discharge port 4Ea while the first housing chamber 4Aa is controlled such that it maintains a predetermined range of positive pressure, whereby the temperature and pressure in the first housing chamber 4Aa is controlled. Moreover, a not shown humidified pad is provided in the first housing chamber 4Aa, and it humidifies by evaporating water to maintain the humidity of the first housing chamber 4Aa in a predetermined range. Additionally, a not shown thermoelectric element, such as a Peltier device, can be housed as heating means in the first lid body 4Ba and each wall of the upper surface, the bottom surface and side surfaces of the first housing chamber 4Aa facing an inner portion of the first housing chamber 4Aa to heat the inner portion of the first housing chamber 4Aa in addition to heating by the gas supplied from the supply port 4Da. By doing this, general heating is achieved by supplying the gas and a fine temperature control is achieved by the heating means, so that a more strict temperature control can be executed. Moreover, dew condensation in each inner surface of the first housing chamber 4Aa can be prevented.

As the article to be housed in the second housing chamber 4Ab related to the harvested sample housed in the first housing chamber 4Aa, a medium used for culturing, an additive, a reagent and the like which are inherent to the donor of the harvested sample housed in the first housing chamber 4Aa can be listed. More specifically, a serum derived from the donor and a medium to which a serum is added can be listed. These samples are stored in a storage container 14 and housed in the second housing chamber 4Ab for refrigerating. Air cooled to about 4° C. or gas such as an inert gas is supplied from the supply port 4Db and discharged from the discharge port 4Eb while the second housing chamber 4Ab is controlled such that it maintains a predetermined range of positive pressure, whereby the temperature and pressure in the second housing chamber 4Ab can be managed. Additionally, as a cooling method of the second housing chamber 4Ab, not limited to a method that a cooling fluid constituted by cooled gas is directly circulated in the second housing chamber 4Ab, piping may be provided from the supply port 4Db to the discharge port 4Eb along the inner wall of the second housing chamber 4Ab to circulate the cooling fluid. In such a case, a cooled liquid or gel may be used as a cooling fluid other than a gas.

Moreover, as shown in FIG. 2, identifying means 15 is provided on each housing part main body 4A of the harvested sample preparation personal box 4 for identifying one from the other. As the identifying means 15, providing a different barcode, ID tug or IC chip for each housing part 4A, reciting different numerals, characters, numbers, symbols and the like, applying different colors and the like may be applied.

The storing means 5 that stores each harvested sample preparation personal box 4 includes housing holes 5A to 5F aligned in a horizontal row on a front surface of the storing means 5 for housing the housing part main body 4A of each harvested sample preparation personal box 4. In an inner portion of each of the housing holes 5A to 5F, a fluid supply pipe 16 to be connected with the supply port 4Da and a fluid discharge pipe 17 to be connected with the discharge port 4Ea of the first housing chamber 4Aa included in each housing part main body 4A are provided, and moreover, a cooling fluid supply pipe 18 to be connected with the supply port 4Db and a cooling fluid discharge pipe 19 to be connected with the discharge port 4Eb of the second housing chamber 4Ab included in each housing part main body 4A are provided.

Additionally, each of the supply pipes 16, 18 and each of the discharge pipes 17, 19 in each of the housing holes 5A to 5F house a not shown on-off valve which is opened when each of the supply ports 4Da, 4Db and each of the discharge ports 4Ea, 4Eb is connected.

In addition, by moving the housing part main body 4A of each harvested sample preparation personal box 4 from the moving means 9 to be housed in the housing holes 5A to 5F, the supply port 4Da of the first housing chamber 4Aa included in the housing part main body 4A is connected with the fluid supply pipe 16, and the discharge port 4Ea is connected with the fluid discharge pipe 17. At the same time, the supply port 4Db of the second housing chamber 4Ab is connected with the cooling fluid supply pipe 18 and the discharge port 4Eb is connected with the cooling fluid discharge pipe 19.

As shown in FIG. 1, each fluid supply pipe 16 disposed in each of the housing holes 5A to 5F communicates with a common fluid supply pipe 23 connected with a fluid supply source 23 and constitutes fluid supply means (culture fluid supply means), and each fluid discharge pipe 17 communicates with a common fluid discharge pipe 25 connected to fluid discharge means 24 and constitutes fluid discharge means.

Moreover, each cooling fluid supply pipe 18 communicates with a common cooling fluid supply pipe 28 connected with a cooling fluid supply source 27 and constitutes fluid supply means (cooling fluid supply means), and each cooling fluid discharge pipe 19 communicates with a common cooling fluid discharge pipe 30 connected to cooling fluid discharge means 29 and constitutes cooling fluid discharge means.

In this embodiment, as described above, by supplying a gas appropriate for cell culture to the first housing chamber 4Aa of each harvested sample preparation personal box 4 and maintaining its atmosphere, the first housing chamber 4Aa functions as an incubator. Moreover, by supplying a cooling gas or other fluid to the second housing chamber 4Ab of each harvested sample preparation personal box 4 and maintaining it atmosphere, the second housing chamber 4Ab functions as a low temperature storage.

With this configuration, it is unnecessary to independently provide electrical components such as a fan included by the conventional incubators and low temperature storages, and the matter that vibration caused by a fan motor or the like affects the culture can be prevented.

An example of operation procedures according to a harvested sample preparation system of this embodiment thus configured will be explained. Additionally, unless otherwise stated, operations which will be explained below are executed by an operator in the preparation operation room 1, and operations in the stocker isolator 2 and the operation isolator 3 are executed through gloves 7.

First, the transfer box 6 is connected with the stocker isolator 2 to communicate with each other, and in a state that the pass-box with decontamination 2A is also in communication, the decontamination apparatus 8 is connected with the stocker isolator to supply a decontamination gas. By this operation, the entire inner portion of the stocker isolator 2, the pass-box with decontamination 2A and the transfer box 6 in a communication state is decontaminated to obtain a sterile condition and the inner portion is maintained at a positive pressure (S1 of FIG. 5). Moreover, at this time, necessary materials, a reagent and the like which are previously delivered in the stocker isolator 2 are also decontaminated.

Figure 5:
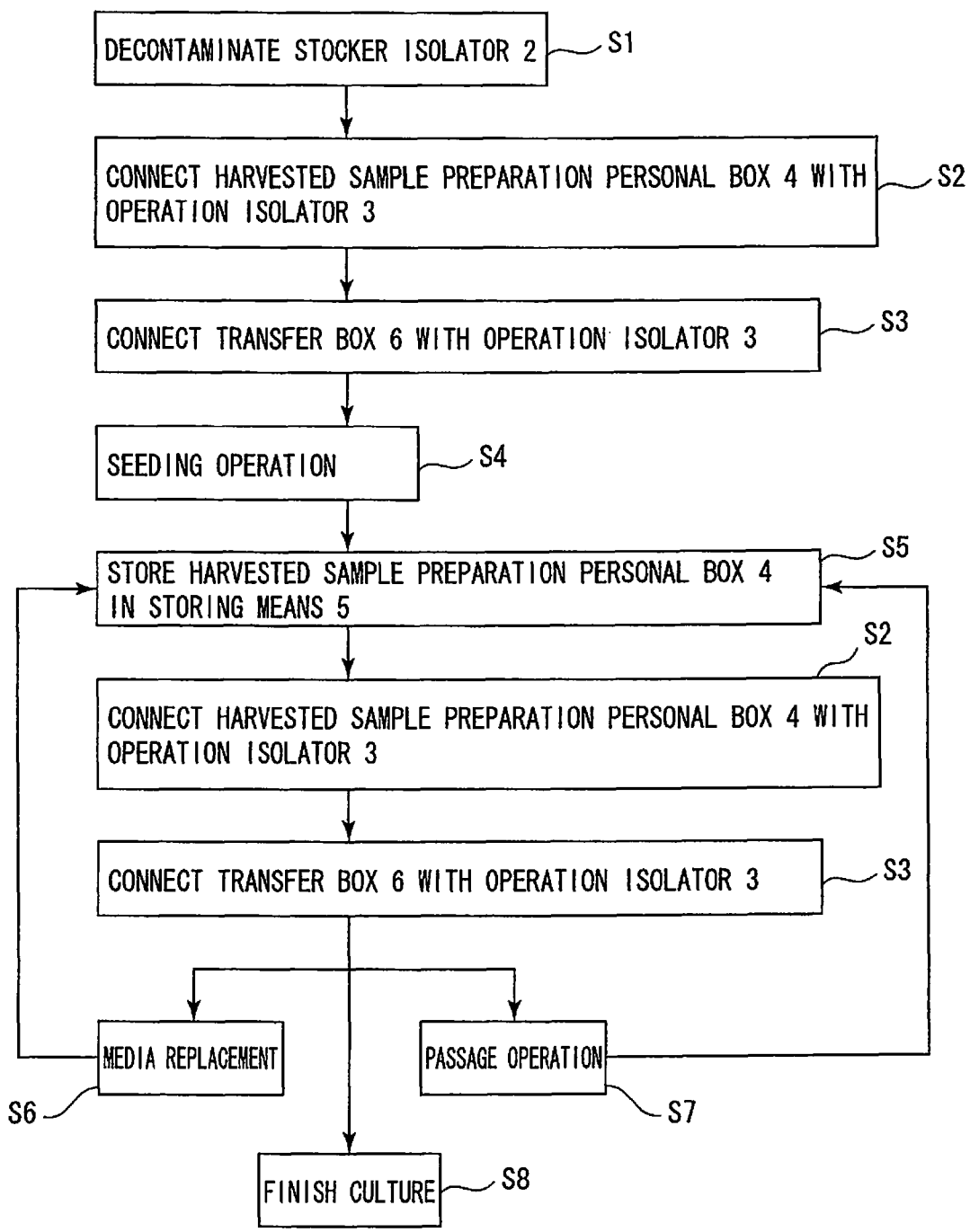
FIG. 5 is a process flowchart of a harvested sample preparation method showing an embodiment according to the present invention.

On the other hand, to the operation isolator 3, after the housing part main body 4A of one harvested sample preparation personal box 4 is connected through the connecting means 4C, the first connection lid 4Ca to which the first lid body 4Ba is fitted and the second connection lid 4Cb to which the second lid body 4Bb is fitted are opened to obtain a communication state, and the decontamination apparatus 8 is connected for supplying a decontamination gas, whereby the entire inner portion in a communication state is decontaminated to obtain a sterile condition and the inner portion is maintained at a positive pressure (S2 of FIG. 5). Additionally, in a state that the housing part main body 4A is thus connected to the operation isolator 3 through the connecting means 4C, each of the supply ports 4Da, 4Db and each of the discharge ports 4Ea, 4Eb are hermetically closed by the cap 12.

In this state, a vessel that houses a harvested sample such as a cell collected from one donor, a vessel that houses an article related to the harvested sample, such as serum derived from this donor, and a vessel that houses a medium are delivered in the stocker isolator 2 after their outer surfaces are decontaminated in the pass-box with decontamination 2A, and they are housed in the transfer box 6. The transfer box 6 housing these vessels are separated from the stocker isolator 2 after they are hermetically sealed and connected with the operation isolator 3 (S3 of FIG. 5), and the articles such as the housing vessels are delivered to the operation isolator 3 while a sterile condition is maintained.

In addition, exterior packages of materials and the like are opened for stocking in the stocker isolator 2, and a necessary number of empty culture vessels 13, the storage container 14 and materials, a reagent and the like which are currently used are simultaneously delivered aseptically to the operation isolator 3 through the transfer box 6.

After that, in the operation isolator 3, a medium is inserted into the delivered culture vessel 13, and with the addition of a serum derived from the donor, the culture vessel 13 is prepared as a medium derived from the donor, and then a cell is seeded to this vessel (S4 of FIG. 5). In addition, the remaining medium is inserted into the storage container 14 with the addition of a serum, and a medium derived from the donor is prepared.

The culture vessel 13 in which the cell is seeded is housed in the first housing chamber 4Aa of the housing part main body 4A of the harvested sample preparation personal box 4 as a harvested sample collected from the single donor. On the other hand, the storage container 14 that houses the medium to which a serum is added is housed in the second housing chamber 4Ab of the housing part main body 4A as an article related to the harvested sample housed in the first housing chamber 4Aa. Moreover, after closing of the first lid body 4Ba and the second lid body 4Bb of the harvested sample preparation personal box 4, the housing part main body 4A is separated from the operation isolator 3 while maintaining its inner sterile condition, and then, after each cap 12 of the supply ports 4Da, 4Db and the discharge ports 4Ea, 4Eb is removed, the housing part main body 4A is housed in the housing hole 5A of the storing means 5, whereby the supply port 4Da and the fluid supply pipe 16, the discharge port 4Ea and the fluid discharge pipe 17, the supply port 4Db and the cooling fluid supply pipe 18, and the discharge port 4Eb and the cooling fluid discharge pipe 19 are respectively connected (S5 of FIG. 5). Additionally, as shown in FIG. 3, by hermetically closing the first connection lid 4Ca and the second connection lid 4Cb, even after the housing part main body 4A is separated, the operation isolator 3 can maintain a hermetically-closed state.

Additionally, the total amount of serums may be added to the storage container 14 that houses a medium in one preparation, or a necessary amount of serums and a medium may be added to the culture vessel 13 for each preparation. In the latter case, the vessel that houses the serums is housed in the second housing chamber 4Ab as the storage container 14 and stored.

When the harvested sample preparation personal box 4 is thus stored in the storing means 5, the cell is cultured in the first housing chamber 4Aa, and in the second housing chamber 4Ab, the donor-derived serum of the cell housed in the first housing chamber 4Aa or the medium to which the serum is added are stored in a low temperature. Due to this, regarding a cell, a serum which is inherent to the cell and a medium to which the serum is added, mix-up between different donors can be prevented. Moreover, management is executed by reading the barcode, ID tug or IC chip as the identifying means 15 of the housing part main body 4A or recording the number, symbols and the like associated with the donor information of the housed harvested sample.

Next, when a cell related to another donor is handled as a harvested example collected from a single donor, the housing part main body 4A of the harvested sample preparation personal box 4 with different identifying means 15 is connected to the operation isolator 3 through the connecting means 4C (S2 of FIG. 5) to obtain a communication state, and the operation isolator 3 and the harvested sample preparation personal box 4 are decontaminated by a decontamination gas. After that, the transfer box 6 is connected with the operation isolator 3 (S3 of FIG. 5), and the current harvested sample, an article related to this harvested sample, the culture vessel 13 and the storage container 14 are delivered into the operation isolator 3 through the transfer box 6.

In this state, a seeding operation is executed as described before (S4 of FIG. 5), the culture vessel 13 in which a cell is seeded is housed in the first housing chamber 4Aa of the housing part main body 4A of the harvested sample preparation personal box 4, and the storage container 14 that houses a medium to which a serum is added is housed in the second housing chamber 4Ab of the housing part main body 4A of the harvested sample preparation personal box 4. After that, the first lid body 4Ba and the second lid body 4Bb are closed and the housing part main body 4A of the harvested sample preparation personal box 4 is separated from the operation isolator 3, and this housing part main body 4A is housed in the housing hole 5B of the storing means 5 (S5 of FIG. 5).

In this way, even while the seeding operation is executed when the housing part main body 4A of another harvested sample preparation personal box 4 is connected with the operation isolator 3, a cell culture of a different donor is continued in the harvested sample preparation personal box 4 in which the culture vessel is previously housed and stored in the storing means 5.

In the storing means 5, carbon dioxide heated to a temperature appropriate for culturing is supplied from the fluid supply source 22 to the first housing chamber 4Aa included by the housing part main body 4A of the harvested sample preparation personal box 4 in each of the storing holes 5A to 5F, and carbon dioxide is discharged from each of the first housing chamber 4Aa to be collected to the fluid discharge means 24. Moreover, a cooling fluid of 4° C. which is appropriate for the storing of a medium is supplied from the cooling fluid supply source 27 to the second housing chamber 4Ab included by the housing part main body 4A of the harvested sample preparation personal box 4 in the housing holes 5A to 5F, and the cooling fluid is collected from each of the second housing chamber 4Ab to the cooling fluid discharge means 29. In this state, cell culturing is executed only during a predetermined period in the first housing chamber 4Aa included by each of the housing part main body 4A stored in the storing means 5, and the donor-derived serum of the cultured cell or the medium to which the serum is added is stored at a low temperature in the second housing chamber 4Ab.

Further, after a predetermined period has elapsed from the above seeding related to the cell in each harvested sample preparation personal box 4, replacement of the media is executed.

In this case, to the operation isolator 3 whose inner portion has already been decontaminated, the housing part main body 4A of the object harvested sample preparation personal box 4 is connected via the connecting means 4C after removal from, for example, the housing hole 5A of the storing means 5 (S2 of FIG. 5), and the transfer box 6 is connected (S3 of FIG. 5) to deliver the necessary material, container, reagent and the like. Then, the first lid body 4Ba and the second lid body 4Bb of the harvested sample preparation personal box 4 are opened, the culture vessel 13 and the storage container 14 are delivered into the operation isolator 3, and after an old medium is removed by suction from the culture vessel 13, a new medium of the storage container 14 is inserted in the culture vessel 13 (S6 of FIG. 5). Thereafter, the culture vessel 13 is housed in the first housing chamber 4Aa of the housing part main body 4A of the harvested sample preparation personal box 4 while the storage container 14 is housed in the second housing chamber 4Ab, and after the first lid body 4Ba and the second lid body 4Bb are closed, connection by the connecting means 4C is cancelled, and then the housing part main body 4A is again housed in the storing means 5 (S5 of FIG. 5). After that, the cell culture is continued.

Moreover, to a cell stored in the harvested sample preparation personal box 4 with a predetermined culture period elapsed in the storing means 5, a passage operation is executed.

In this case, to the operation isolator 3 whose inner portion has already been decontaminated, the housing part main body 4A of the object harvested sample preparation personal box 4 is connected via the connecting means 4C after removal from, for example, the housing hole 5A of the storing means 5 (S2 of FIG. 5), and the transfer box 6 is connected (S3 of FIG. 5) to deliver an unused culture vessel 13. Then, the culture vessel 13 and the storage container 14 are delivered to the operation isolator 3 from the housing part main body 4A.

Thereafter, after a medium is inserted from the storage container 14 to the new culture vessel 13, a part of the culturing cells is moved from the currently-culturing vessel 13 (S7 of FIG. 5). In this way, an increased number of culture vessels 13 by a passage operation are housed in the first housing chamber 4Aa of the housing part main body 4A of the harvested sample preparation personal box 4 and the storage container 14 is again housed in the second housing chamber 4Ab, and the housing part main body 4A is again stored in the storing means 5 (S5 of FIG. 5). After that, the cell culture is continued.

Additionally, in the above operation procedures, in a cell preparation step for a single donor, while one seeding operation is executed in one step, a media replacement operation and a passage operation are executed several times in one step. For example, the passage operation is executed every four to six days, and the media replacement operation is executed between the seeding operation and the passage operation or between the passage operations every two or three days, for example. Even during any harvested sample preparation personal box 4 is connected to the operation isolator 3 for these media replacement operation and passage operation, cell culture is continued in other harvested sample preparation personal boxes 4.

Thereafter, necessary passage and media replacement are repeated, and when the culture is finished after a desired period is elapsed, the housing part main body 4A of each harvested sample preparation personal box 4 housing the culture vessel 13 and the storage container 14 is sequentially removed from the storing means 5 and connected with the decontaminated operation isolator 3 via the connecting means 4C (S2 of FIG. 5) to deliver the culture vessel 13 into the operation isolator 3. Moreover, the transfer box 6 is connected with the operation isolator 3 (S3 of FIG. 5) to deliver a vessel for housing the cultured cell into the operation isolator 3, and the cultured cell is transferred from the culture vessel 13 to other containers. After that, a decontaminated gas is supplied from the decontamination apparatus 8 to the operation isolator 3, and external surfaces of the harvested sample preparation personal box 4, the culture vessel 13, the storage container 14 and the vessel housing the cultured cell are decontaminated by the decontamination apparatus 8 and the decontaminated articles are delivered from the operation isolator 3 (S8 of FIG. 5).

As stated above, in the harvested sample preparation system according to the present invention, one harvested sample preparation personal box 4 can be managed by the unit of a donor as a personal box used by one donor. Moreover, since the culture vessel 13 in which a cell collected from one donor is seeded and the storage container 14 housing a serum which is inherent to the cell or the storage container 14 housing a medium to which the serum is added are stored in one harvested sample preparation personal box 4, a mix-up is prevented, and further, since an inner portion of the operation isolator 3 is previously decontaminated for each connection of the harvested sample preparation personal box 4 of a different donor, the resulting cross-contamination can be prevented.

Moreover, since there is no electric part in the harvested sample preparation personal box 4, no adverse effect caused by vibration of electric parts is provided on a harvested sample such as a cell which is cultured in the first housing chamber 4Aa, and the harvested sample preparation personal box 4 is lightweight and easily portable. Moreover, with the state that the operation isolator 3 is connected with the harvested sample preparation personal box 4, the first housing chamber 4Aa and the second housing chamber 4Ab of the harvested sample preparation personal box 4 can be decontaminated at one time.

Moreover, according to the harvested sample preparation system of the present invention, the harvested sample preparation personal box 4 itself can be manufactured reasonably and can easily deal with a number of donors. Moreover, it includes the fluid supply source 22 for supplying fluid to a plurality of harvested sample preparation personal boxes 4 and the cooling fluid supply source 27 for supplying cooling fluid to the plurality of harvested sample preparation personal boxes 4, and an increase of the number of donors can be addressed by increasing the number of harvested sample preparation personal boxes 4, so that a harvested sample preparation system dealing with a number of donors can be easily established.

Additionally, this embodiment is on the premise that the above media replacement operation and the like is executed by an operator in the preparation operation room 1; however, an operation robot may be installed on the stocker isolator 2 to automate a delivery operation of the material and the like by this operation robot. Moreover, automatic attachment and removal means and automatic moving means of the transfer box 6 and each harvested sample preparation personal box 4 may be provided to automate an attachment and removal operation and a moving operation of the transfer box 6 and each harvested sample preparation personal box 4.

REFERENCE SIGNS LIST

2: stocker isolator
3: operation isolator
4: harvested sample preparation personal box
4A: housing part main body
4Aa: first housing chamber
4Ab: second housing chamber
4B: lid body
4Ba: first lid body
4Bb: second lid body
4C: connecting means
4Ca: first connection lid
4Cb: second connection lid
5: storing means
13: culture vessel
14: storing container
15: identifying means

The invention claimed is:

1. A harvested sample preparation system comprising:
an isolator in which aseptic manipulation is executed, the isolator having an aperture formed on a wall and a connection lid that hermetically closes the aperture;
a harvested sample preparation personal box having a first housing chamber for housing a culture vessel in which a harvested sample collected from a single donor is seeded, a second housing chamber for housing an article related to the harvested sample housed in the first housing chamber, and a lid body hermetically closing the first and second housing chambers and capable of being integrated with the connection lid of the isolator; and
storing means for storing a plurality of personal boxes and having culture fluid supply means for providing a fluid appropriate for culturing and cool fluid supply means for supplying a cool fluid,
wherein the isolator, the personal box, and the storing means are kept in preparation workrooms that are maintained at respectively predetermined degrees of purity,
when the isolator and the personal box are connected and the integrated lid body and connection lid are opened, the isolator communicates with the first and second housing chambers to house the culture vessel in the first housing chamber from the isolator and to house the article related to the harvested sample in the second housing chamber, and
when the personal box separated from the isolator is stored in the storing means, the culture fluid supply means supplies the fluid appropriate for culturing to the first housing chamber to culture a harvested sample in the first housing chamber, and at the same time, the cool fluid supply means supplies the cool fluid to the second housing chamber to refrigerate the article related to the harvested sample in the second housing chamber.

2. A harvested sample preparation method comprising the steps of:
preparing a plurality of harvested sample preparation personal boxes including a plurality of independent closed spaces hermetically sealable by a lid body;
connecting any of the harvested sample preparation personal boxes with an isolator in which aseptic manipulation is executed to integrate the lid body of the harvested sample preparation personal box with a connection lid that hermetically closes an aperture formed on a wall of the isolator;
opening the integrated lid body and connection lid to communicate the isolator with the closed space;
housing a culture vessel in which a harvested sample collected from a single donor is seeded in at least one closed space;
housing an article related to the housed harvested sample in another closed space;
separating the harvested sample preparation personal box from the isolator;
storing the harvested sample preparation personal box in storing means;
by the storing means, supplying fluid appropriate for culturing to the closed space that houses the culture vessel in the harvested sample preparation personal box to culture the harvested sample;
providing a cool fluid to the closed space that houses the article related to the harvested sample to refrigerate the article;
decontaminating an inner portion of the isolator after the isolator is separated from the harvested sample preparation personal box; and
connecting a different harvested sample preparation personal box with the isolator to handle a harvested sample collected from a different donor.

* * * * *